United States Patent [19]

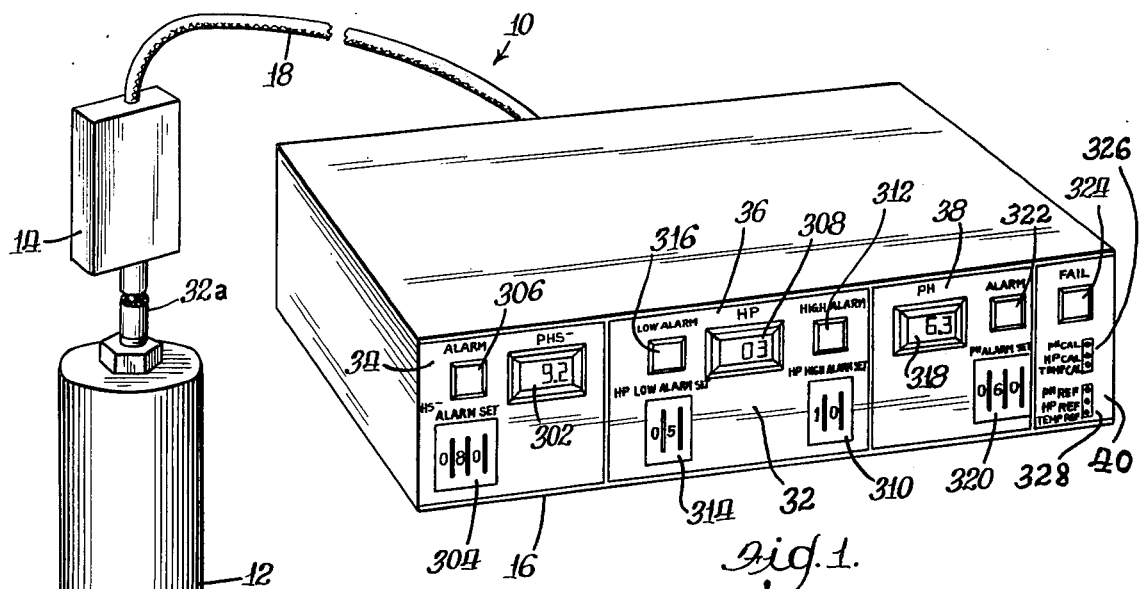
Fig. 1.
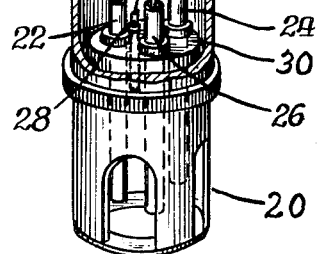
Fig. 2.
$$S_T = H_2S + HS^- + S^=$$
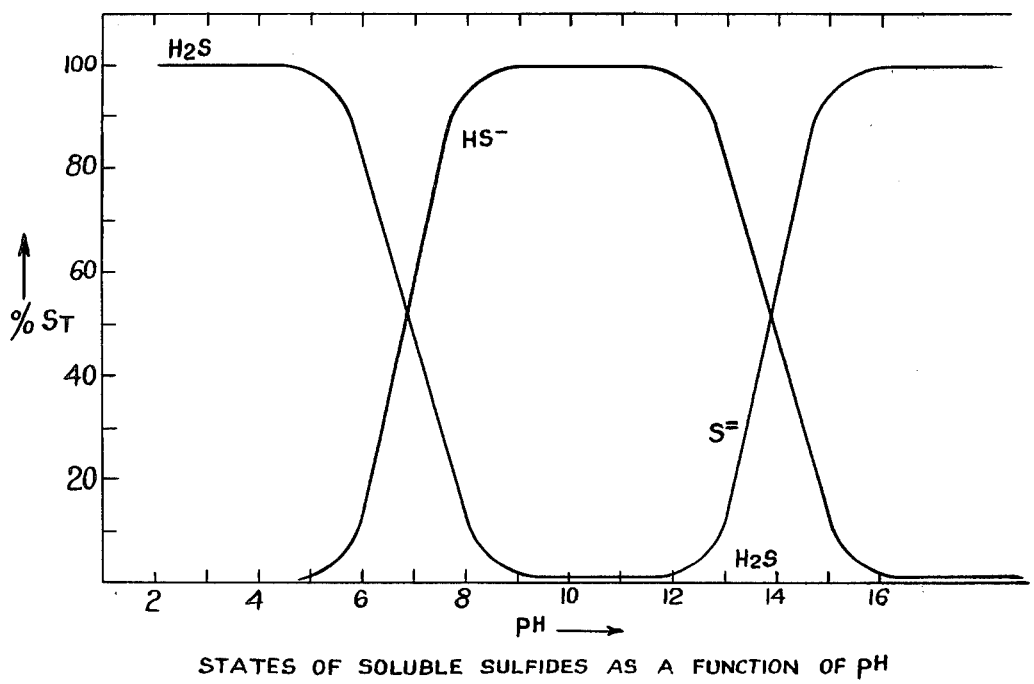
STATES OF SOLUBLE SULFIDES AS A FUNCTION OF pH

Zetter

[11] 4,154,659
[45] May 15, 1979

[54] SULFIDE MONITORING SYSTEM AND METHOD

[75] Inventor: Mark S. Zetter, Santa Clara, Calif.

[73] Assignee: Dalphian Corporation, Los Altos, Calif.

[21] Appl. No.: 829,072

[22] Filed: Aug. 30, 1977

[51] Int. Cl.² ............................................. G01N 27/56
[52] U.S. Cl. .............................. 204/1 T; 23/230 EP; 73/153; 204/195 R; 324/29; 324/30 R
[58] Field of Search ................... 204/1 F, 1 H, 195 R; 324/29, 30 R; 23/230 EP; 73/153

[56] References Cited

U.S. PATENT DOCUMENTS 3,702,235  11/1972  Fallgatter ..................... 23/230 EP X
3,915,831  10/1975  Riseman et al. .................. 204/195 P Primary Examiner—G. L. Kaplan
Attorney, Agent, or Firm—Fitch, Even & Tabin

[57] ABSTRACT

Methods and apparatus relating to systems for determination of sulfide species and hydrogen sulfide hazard potential of well drilling mud.

10 Claims, 8 Drawing Figures

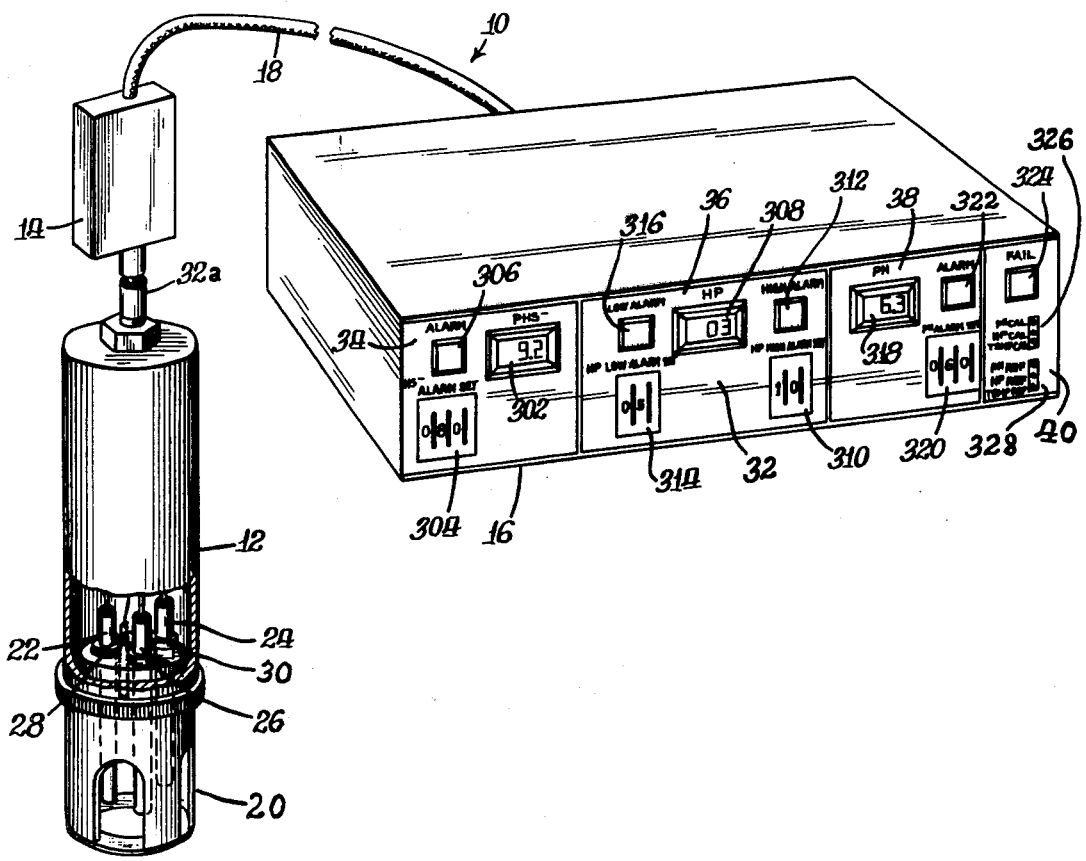

SULFIDE MONITORING SYSTEM AND METHOD

The present invention is directed to methods and apparatus for making electrochemical measurements, and, more particularly, is directed to such methods and apparatus which are particularly adapted for sulfide determinations in environments such as well drilling muds.

Remote sensing or measurement of potentially lethal materials such as hydrogen sulfide is desirable for purposes of corrosion control and personnel protection in environments such as oil drilling environments where hydrogen sulfide deposits or strata may be encountered during drilling operations. The hydrogen sulfide thus encountered may not only have a deleterious effect on equipment, but may be transported to the surface in the drilling mud where it may be released into the ambient temperature.

Conventionally, hydrogen sulfide presence in the drilling mud may be measured by air sensors, but such sensors have the disadvantage of being dependent upon wind direction, and do not necessarily measure the potential hazard from hydrogen sulfide presence in the drilling mud. Conventional aqueous sulfide measuring apparatus may not directly provide the appropriate information as to potential hazards or a desired sulfide species such as hydrosulfide concentration. Further, conventional aqueous sulfide measuring apparatus may not be capable of prolonged remote sensing operation in a drilling rig environment. Thus, improved methods and apparatus for measuring and determining the potential hydrogen sulfide hazard, and the hydrosulfide concentration in well drilling mud would be desirable.

Accordingly, it is an object of the present invention to provide such improved methods and apparatus. It is a further object of the invention to provide such methods and apparatus which may be particularly adapted for operation in hostile or difficult sensing environments. It is a further object of the present invention to provide such methods and apparatus which provide accurate measurements over a range of temperatures and operating conditions encountered in drilling operations.

These and other objects of the invention will become apparent upon consideration of the following detailed description and the drawings of which:

FIG. 1 is a perspective view of an embodiment of apparatus in accordance with the present invention;

FIG. 2 is a graph showing the relationship between sulfide ion species and pH in aqueous solution;

Figure 3:
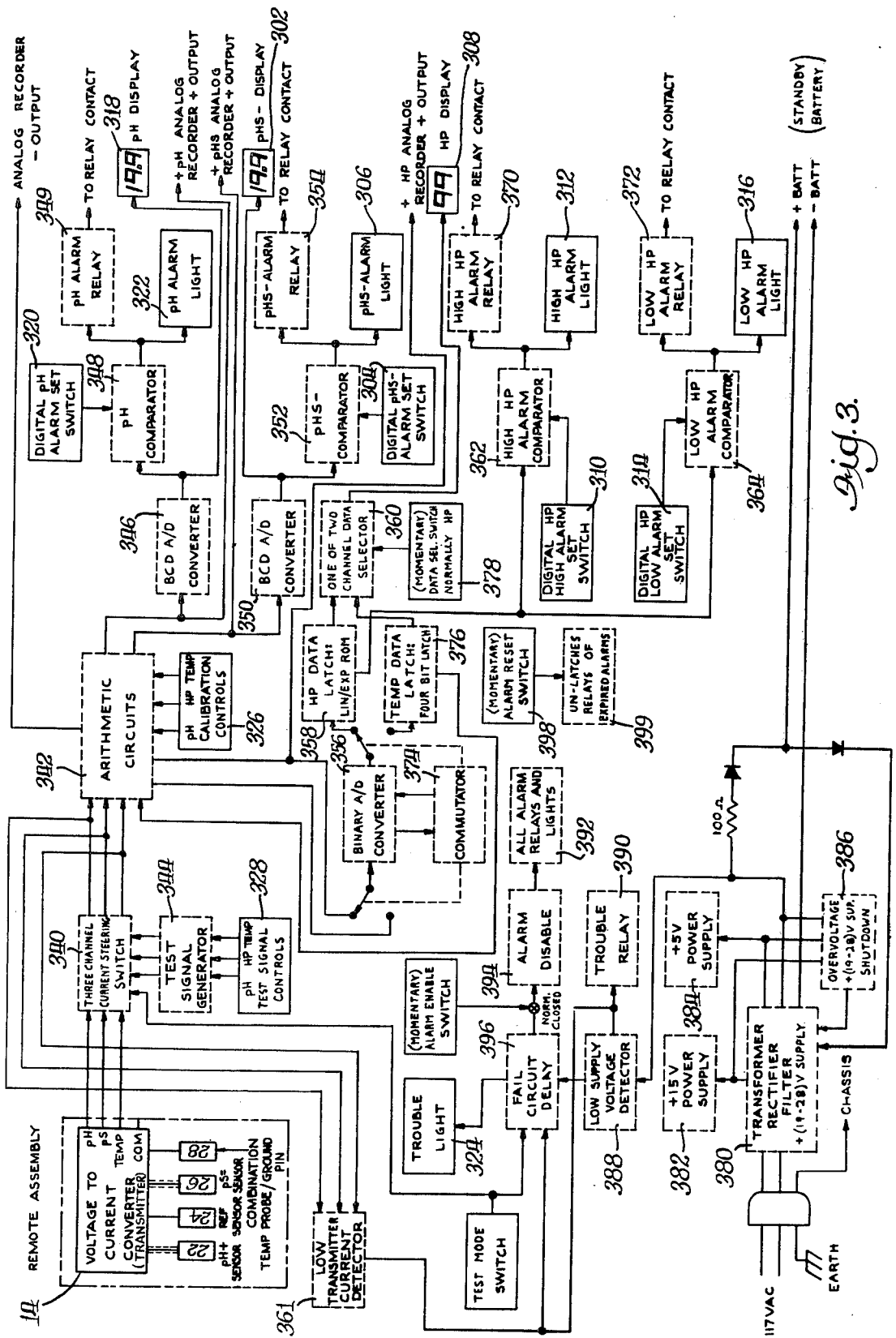
FIG. 3 is a block diagram of the various circuit elements of the apparatus of FIG. 1.

Generally, the present invention is directed to mud monitoring systems for sulfide corrosion control and personnel protection for use on drilling rigs where sulfide bearing deposits and strata may be encountered.

Various aspects of the invention concern methods and apparatus for measuring the concentration of hydrosulfide ion [$HS^-$], and methods and apparatus for determining the hydrogen sulfide hazard potential of hydrogen sulfide dissolved in the drilling mud, by determining the hydrogen sulfide gas concentration which would be in gaseous equilibrium with a soluble sulfide containing solution. The present disclosure is also directed to temperature compensation circuitry for electrochemical potential signal processing, and is further directed to high impedance electrochemical electrode systems having a grounding current path for measuring hydrogen ion and sulfide ion concentration in a grounded conductive solution. As indicated, various features of the present invention concern hydrosulfide ion measuring systems. In accordance with the present invention, such systems are provided which comprise hydrogen ion selective electrode means for providing an output signal having an electrochemical potential which is a function of hydrogen ion concentration, sulfide ion selective electrode means for providing an output signal having an electrochemical potential which is a function of sulfide ion concentration [$S^=$], and means for combining a signal representative of the electrical potential of the hydrogen ion electrode means and a signal representative of the electrical potential of the sulfide ion electrode means in a ratio of hydrogen ion potential to sulfide ion potential of about 1:2 to provide a difference output signal which varies as a function of the hydrosulfide ion concentration. The apparatus (or methods) may further utilize means for combining a signal representative of a predetermined electrochemical potential reference value with the sulfide ion representative signal and the hydrogen ion representative signal, such that the said difference output signal is proportional to hydrosulfide [$HS^-$] ion electrochemical potential. The electrochemical reference value may generally be provided by means of a reference electrode.

In connection with aspects relating to the determination of the potential hazard in respect of hydrogen sulfide gas concentration, methods and apparatus are provided for determining a hydrogen sulfide gas concentration which could be in gaseous equilibrium with an aqueous sulfide solution. Such methods and apparatus may utilize the electrochemical potential output of hydrogen ion selective electrode means and sulfide ion selective electrode means such as described in connection with the hydrosulfide determining methods and apparatus. The hazard potential systems further utilize means for combining a signal representative of the sulfide electrode potential with a signal representative of the hydrogen ion electrode potential, to provide a difference output signal which varies as a function of the gaseous hydrogen sulfide equilibrium concentration which could exist in equilibrium with the aqueous sulfide solution being measured. Such hydrogen sulfide hazard potential determining systems may further include means for combining a signal representative of a predetermined electrochemical reference potential value with the sulfide ion representative signal and the hydrogen ion representative signal such that the difference output signal is proportional to the gaseous hydrogen sulfide equilibrium concentration which would exist in equilibrium with the aqueous sulfide solution.

As also indicated, various aspects of the present disclosure concern temperature compensation in electrochemical measurement systems, and particularly in systems in which electrochemical potentials are sensed remotely from signal processing and/or temperature compensation locations. Such temperature compensation systems make use of the isopotential point of the electrochemical system under measurement, and further utilize digitized amplifier gain circuitry comprising an operational amplifier means for providing an output signal current at an output terminal which is proportional to the potential difference between a reference input terminal and a signal input terminal, means for providing a temperature dependent electrochemical potential signal having an isoelectric point at which the value of the signal does not substantially vary with temperature, and means for providing a digital value of the measurement temperature. The compensation system further comprises means for providing a voltage to said reference terminal substantially corresponding to the value of the isoelectric point, input resistance means for providing an electrically resistive circuit between the electrochemical signal means and the input terminal, and feedback resistance means for providing an electrically resistive circuit between the input terminal and the output terminal such that the ratio of the voltage potential at said output terminal to the voltage potential of the temperature and species concentration dependent signal substantially corresponds to the ratio of the resistance of said feedback means to the resistance of said input resistance means. At least one of the resistance means should comprise a plurality of discrete resistance elements selectively switchable to provide discrete predetermined variation of said resistance ratio, and through the provision of means for interconnecting these resistance elements in a predetermined manner such that the resistance ratio is incrementally changed with temperature, the output voltage may be compensated so that it is not substantially temperature dependent at all species concentrations.

As indicated, aspects of the present disclosure concern potentiometric electrochemical electrode systems for measuring hydrogen ion and sulfide ion concentration in a grounded conductive solution. Remote sensing in grounded solutions such as well drilling mud also presents difficulties with respect to leakage currents and system grounding, which may produce undesired sensing electrode currents (e.g., through rectification at the active electrode-solution interface). Such difficulties may cause inaccurate readings, change electrode characteristics and produce long-term drifting. Electrode systems adapted to alleviate such problems are provided comprising a pH electrode, a specific ion sulfide electrode, and a reference electrode, and means in electrically conductive relationship with said electrodes for measuring potential between pairs of said electrodes, which is capable of being at a dc or ac potential with respect to the solution. The electrode system further includes grounding pin means in electrically conductive relationship with the electrodes and grounded conductive solution, for preventing ac or dc current due to said potential from flowing through any of said electrodes between said measuring means and said conductive solution by providing a path for said current to said conductive solution, the ratio of the impedance of the current path for said ac and dc current through the lowest impedance electrode path, to the impedance of said ground pin current path being at least about 100 and preferably at least about 1000.

Turning now to the drawings, the previously described aspects of the present disclosure, and various of the aspects, will now be described in detail with respect to the embodiment of apparatus illustrated in FIGS. 1, 3-4 of the drawings.

As illustrated in FIG. 1, the specific embodiment 10 of the apparatus comprises a sensor and housing unit 12, a transmitter unit 14, and a controller unit 16. The transmitter unit 14 and the control unit 16 are connected by means of a four-conductor cable 18.

The sensor and housing unit 12 comprises a housing 20 for a hydrogen ion selective (pH) electrode 22, a reference electrode 24, sulfide ion selective electrode 26, and a combination temperature sensor/ground pin element 28. The active sensing portions of the electrodes, sensor and ground pin are disposed in a zone of the housing 20 which leaves the sensors open to the environment, but protects them from mechanical damage, while the electrical terminal connection ends of these elements project through seals into a hermetically sealed zone 30 of the housing 20 in accordance with conventional practice. In use, the sensor housing will generally be mounted in a location that is filled with drilling mud during normal drilling operations, and will be located as close to the mud flow line discharge as possible, because the closer the sensor unit is to the discharge point, the sooner sulfide and pH changes will detected by the apparatus 10. In this connection, the sensor may be located either in the "possum belly" or in the mud tank directly below the shale shaker in a conventional drilling mud circulation system. Of course, the housing should be mounted so that it will not become buried in cuttings that settle to the bottom, and the transmitter assembly 14 should not become submerged when the mud is at its highest level. Accordingly, sealed conduit 32a of desired length (shown broken away in the drawing to indicate variable length) may be provided between the housing 12 and the transmitter unit 14 to shield the electrical cable connections between the transmitter 14 and the electrodes, ground pin and temperature sensor.

The electrodes 22, 24, 26 develop electrochemical potential voltages, and the temperature sensor 28 also develops voltage potential information through an appropriate resistance mechanism. The transmitter unit 14 converts the voltage potential information of the electrodes and temperature sensor to variable current signals, and transmits these signals by means of cable 18 to the controller 16 for appropriate processing and display. The varying voltage information is converted to correspondingly varying current information so that it may be transmitted over the cable 18 (which may be 1000' or more in length). The transmitter 14 comprises a plurality of high-impedance, constant-current, voltage-to-current conversion circuits, and the power to drive the voltage-to-current conversion circuitry of the transmitter 14 is obtained from the control unit as will be more fully described. At the control unit 16 at which the transmitter signals are received and processed, the processed information is displayed on a display panel as shown in FIG. 1. The control unit 16 display panel 32 comprises a hydrosulfide ion [HS$^-$] display section 34, a hazard potential display section 36, a pH display section 38, and a system reference and calibration section 40.

The hydrosulfide ion display section 34 displays the concentration of hydrosulfide ion as the negative log of the concentration (pHS$^-$ notation), and comprises a digital pHS$^{31}$ display element 302, a digital pHS$^-$ alarm set switch element 304, and an alarm light 306 which is activated when the pHS$^-$ concentration exceeds the value of the alarm set switch 304. The display can show values of pHS$^-$ from 00.0 to 19.9. However, concentrations below that indicated by a pHS$^-$ of about 5.0 are so small that the readings may be utilized primarily only to indicate trends of concentration changes. The pHS⁻ digital alarm set switch 304 may be used to set an alarm point anywhere from pHS⁻=00.0 to pHS⁻=19.9. A pHS⁻ alarm relay and the pHS⁻ alarm lamp 306 are both activated whenever the pHS⁻ display reading is equal to or numerically smaller than the number of the pHS⁻ digital alarm set switch such that the alarm is activated when a preset concentration of HS⁻ is equalled or exceeded (pHS⁻ numbers decrease as the concentration of HS⁻ increases). As a safety feature, this alarm (like all alarms on the instrument) requires manual resetting.

The hazard potential display section 36 displays the concentration, in parts per million, of hydrogen sulfide gas which could exist in equilibrium with the mud sensed by the electrodes. This generally corresponds to the concentration of $H_2S$ which could exist directly above the mud in still air. The display section 36 comprises a digital hazard potential display element 308, a digital high alarm set switch 310 with high alarm light 312 which is activated when the hazard potential reading exceeds the value of the high alarm set switch 310, and a digital low alarm hazard potential set switch 314 with corresponding hazard potential low alarm light 316 which is activated when the hazard potential exceeds the value of the digital alarm set switch 314.

The digital hazard potential (HP) display 308 indicates $H_2S$ gas equilibrium concentration values from 00 to 99 ppm. Should a concentration higher than 99 ppm be measured, the HP display will blink "99" to indicate that the apparatus 10 is out of range. A small flashing "0" can also appear to the left of the HP reading to indicate that the sensor is being operated outside of its predetermined temperature range (or if the "temperature" or "common" cable connection to the transmitter and/or temperature sensor is open circuited). The digital high and low HP alarm set switches 310, 314 are thumb wheel switches used to set alarm points from HP=00 to HP=99. The low HP alarm relay and the low HP alarm lamp 316 are both activated whenever the HP display reading is equal to or greater than a number which may be manually applied to the HP digital low alarm set switch 314. The high HP alarm set switch 310 works identically to the low HP alarm switch 314.

The HP low alarm lamp fixture 316 is a combination lamp and switch; the lamp is activated when the HP low alarm relay is energized. When the switch portion of this fixture is depressed, it over-rides the alarm inhibit circuit that is in operation when the instrument is in the test mode, which will be subsequently described.

The HP high alarm lamp fixture 312 similarly is a combination lamp and switch. The lamp element is activated when the HP high alarm relay is energized. The switch portion may be depressed to cause the HP display 308 to indicate the binary coded temperature range in which the temperature sensor is operating.

The pH display section 38 similarly comprises a digital pH display element 318, together with a digital pH alarm set switch 320 and a pH alarm light 322 which is activated when the measured pH is lower than the value of the pH alarm set switch 320. The digital pH display indicates the hydrogen ion concentration at the pH electrode 22. The digital pH alarm set switch 320 is adapted to permit the setting of an alarm point in the display range from pH=00.0 to pH=19.9. The pH alarm relay and the pH alarm lamp 322 are both activated whenever the pH display reading is equal to or numerically smaller than the pH digital alarm set point.

The pH alarm lamp fixture 322 also is a combination lamp and switch. The lamp portion is activated whenever the pH alarm relay is energized, and the switch portion is the alarm reset switch for all of the alarm circuits (including the pHS⁻, pH, and low and high HP alarms).

The system calibration display and control section 40 comprises a system failure or trouble light 324, together with calibration controls 326 and reference controls 328. The fail lamp fixture 324 is similarly a combination lamp and switch. The lamp is activated (1) when there is an open circuit in the cable 18 or to the sensors 22, 24, 26, 28; (2) when the line or battery voltage to the controller unit 16 is below a predetermined value; (3) when the test switch associated with the fail light fixture 324 is depressed; or (4) for a period of about 60–120 seconds either after the instrument has been turned on, or after any of the above conditions has been rectified. When the fail lamp 324 is activated, all alarm relay and indicator lamp circuits are deactivated.

Test readings for the hazard potential, pH and the temperature code can be introduced by depressing the test mode switch and set, respectively, by adjusting the three adjustment pots labeled "pH ref", "HP ref", and "temp ref" of controls 328. pHS⁻ and HP are interrelated with pH as will be more fully explained hereinafter. Particularly, if the instrument will normally be operating for long periods of time below the limits set for alarm activation, the test instrumentation features permit checking the operability of the alarm lights, displays and external warning systems. However, these features do not test the electrodes and temperature sensors, which are checked by an appropriate calibration procedure utilizing a suitable calibration solution of known pH, hazard potential and temperature and the calibration controls 326 including three pots correspondingly labeled pH Cal, HP Cal, and Temp Cal.

A block circuit diagram of the apparatus 10 is shown in FIG. 3 of the drawings, with previously described functional circuit elements of the front panel of the instrument shown as solid blocks in functional interrelationship with other circuit elements shown as dashed blocks. In FIG. 3, it may be seen that the electrochemical potential pH, reference and sulfide electrode signals 22, 24, 26 are converted to corresponding pH and pS⁼ current signals, as is the IR voltage drop across the temperature probe 28, by the voltage-to-current converter elements of the transmitter. The resultant current pH, pS⁼ and temperature information signals are respectively conducted by lines of the cable 18 to three channel current steering switch 340, which under the control of the test mode switch element of fail light 324, directs either the actual pH, pS⁼ and temperature signals or a simulated set of such signals from test signal control element (reference pots) 328 and test signal generator 344, to arithmetic circuit element 342. The arithmetic circuit element 342 calibrates (with appropriate input from calibration controls 326), processes and compensates the actual or synthetic pH, pS⁼, and temperature signals to produce output signals for pH, pHS[31] and hazard potential (HP).

The compensated pH signal is directed to a conventional binary coded decimal analog to digital converter (BCD A/D) element 346 for direct digital conversion of the signal. The digital pH output signal is directed to the pH display 318, and to pH comparator 348 which compares the digital pH value with the digital alarm set switch for activation of the pH alarm relay 349 for the alarm light 322.

The compensated analog pHS⁻ signal from the arithmetic processor 342 similarly is directed to a conventional BCD A/D circuit element 350 for binary pHS⁻ display 302. Similarly, the digital pHS⁻ value is compared with the value of digital pHS⁻ alarm set switch 304 by pHS⁻ comparator 352 for appropriate activation of pHS⁻ alarm relay 354 and pHS⁻ alarm light 306.

The units of the compensated pH signal, are defined as the negative $\log_{10}$ of the concentration of hydrogen ions, in moles/liter. The corresponding units of the compensated pHS⁻ signal are defined as the negative $\log_{10}$ of the concentration of HS⁻ ions in percent, where the HS⁻ percentage is normalized in terms of one gram HS⁻ per 100 cc of solution being defined as one percent HS⁻. The logarithmic "p" representation is desirable in view of the wide range of H⁺ and HS⁻ concentrations which may be encountered by the instrument.

The compensated hazard potential signal derived by the arithmetic circuits from the pH, PS⁼ and temperature information, as indicated previously represents an equilibrium value of the $H_2S$ gas which could exist in the ambient atmosphere in equilibrium with the mud or other aqueous system under measurement (it is not a direct measurement of ambient $H_2S$ gas) and thus is a valuable representation of the potential immediate hazard in respect of mud sulfide content. The compensated analog hazard potential signal from the arithmetic circuitry 342, like the pH and pHS⁻ signal is in logarithmic (base 10) form. For appropriate display as ppm $H_2S$, the signal is directed to binary analog/digital converter 356, the resulting binary data from which is stored in HP data latch circuit 358 which also includes a linear-exponential read-only memory look-up table for digital conversion of the initally resulting logarithmic binary data to a linear digital ppm representation.

The digital data from the HP latch circuit 358 when (normally) selected by the two channel selector 360, is directed to the HP display 308, and is directed to high and low HP comparators 362, 364 for comparison with the respective values of the HP set switches 310, 314 for activation of high and low HP relays 370, 372 and alarm lights 312, 316.

The arithmetic circuit element 342 utilizes digitalized temperature compensation and requires digital temperature information. Thus, the analog temperature signal is directed to A/D converter 356 which for purposes of efficiency is the same A/D converter used for the HP data signal. Commutator 374 accordingly is used to alternately select in seriatim the HP or temperature analog signal input to A/D converter 356, and to direct the resulting binary data to the appropriately corresponding latch storage element. In this connection, the four-bit binary temperature data is directed to and stored at temperature data latch 376, from which it is made available to the arithmetic circuits 342, and for display in octally coded form at HP display 308 through selector 360 by means of select switch 378.

As shown in FIG. 3, the apparatus 10 also comprises various other generally conventional circuit elements including power supply and trouble-fail circuit elements 380, 382, 386, 388, 390, 394, 396, 398, 399.

Figure 4:
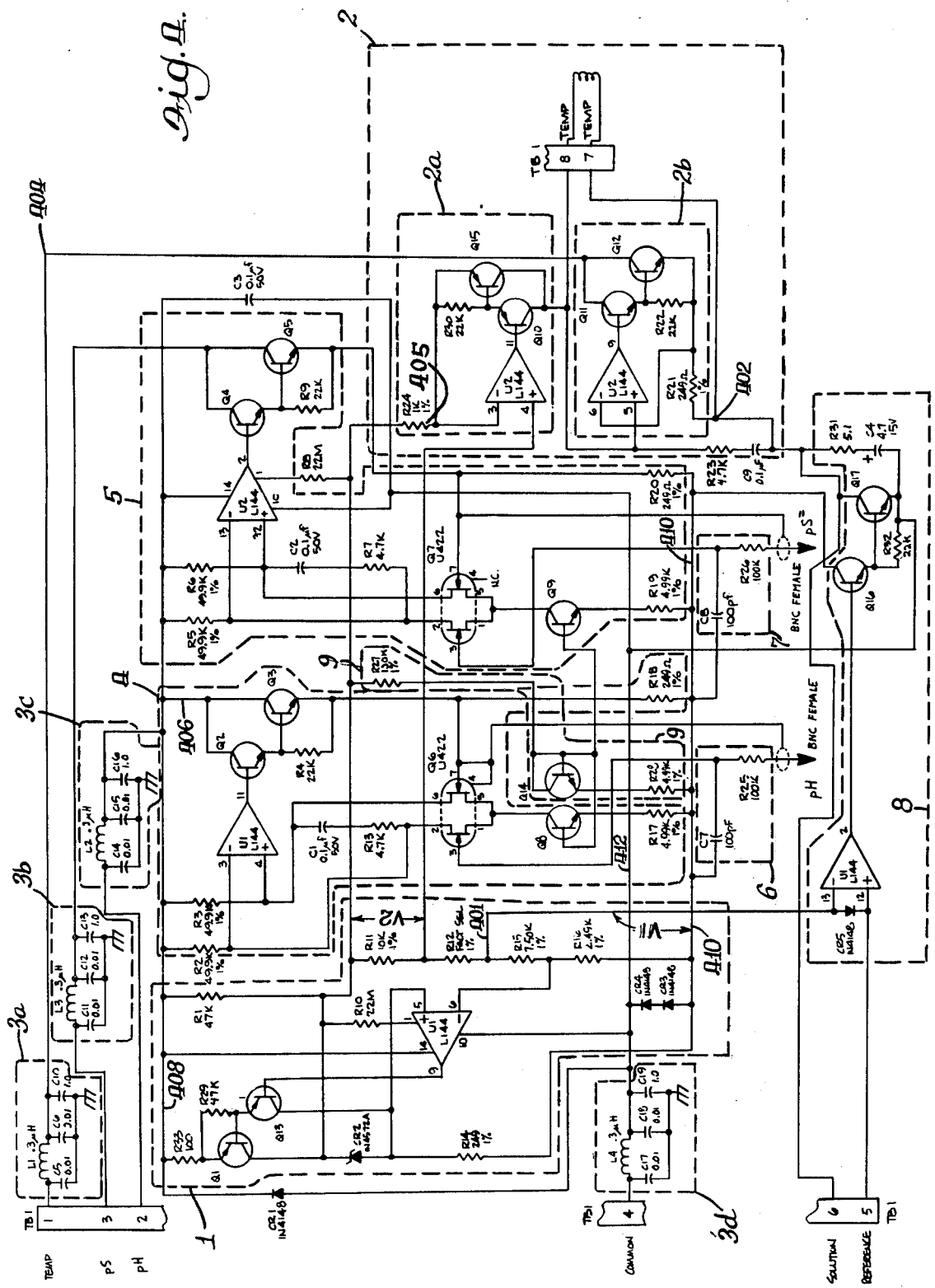
FIG. 4 is a circuit diagram of the electrode and transmitter circuitry of the apparatus of FIG. 1.

FIG. 4 is a circuit diagram of the transmitter remote assembly 14 which receives the voltage potential signals from the pH, reference and pS⁼ electrodes 22, 24, 26 and the temperature probe section of the pin 28, and converts these signals to current representation of pH, pS⁼ and temperature signals for transmission to control unit 16. Only the cable connections to the electrodes are shown in FIG. 4, it being understood that conventional pH electrodes (such as Sensorex S 200 G pH electrodes), pS⁼ electrodes (such as Orion 94-16A, sulfide ion selective electrodes) and reference electrodes (such as Sensorex S 200 RD double junction standard chloride reference electrodes) may be used.

The transmitter circuitry of FIG. 4 comprises voltage supply and system common circuit 1, temperature voltage-to-current converter circuit 2 (comprising subcircuits 2a, 2b), rf filter circuits 3a, 3b, 3c, 3d, pH electrode voltage-to-current converter circuit 4, pS⁻ electrode voltage-to-current converter circuit 5, input rf filter circuits 6 and 7 for circuits 4, 5 and reference electrode circuit 8 and constant bias current circuit 9 for circuits 4 and 5. The transmitter circuitry also provides for a low impedance current path to the grounded solution (mud) via the ground pin section of the temperature sensor element 28 of the housing 12.

As indicated, the remotely locatable transmitter 14 draws all its power from the controller unit. However, because it is desirable to limit the number of wires in the cable 18, the transmitter is of particular design to utilize data transmission wires in the transmission of power from the controller. In this connection, it will be noted that there are only three separate information transmission wires, respectively, for the analog pH, pS⁼ and temperature current signals, and a common return line. In order to effectively accomplish the power transmission and provide for efficient interpretation of the three information channel signals, the voltage-to-current conversion circuits 2, 4, 5 are each adapted to draw a substantially constant amount of current for circuit utilization. The constant currents may be added to variable data currents drawn over the individual data lines, and appropriate compensation may be made at the controller to compensate for the constant current addition to the data signals. The constant currents utilized by the voltage-to-current converters 2, 4, 5 and the variable pH, pS⁼ and temperature representative current signals drawn by the voltage-to-current converters 2, 4, 5 over the respective data lines are summed and returned to the controller via the common return line. Because the pH signal has the largest current sensitivity, the constant currents used by each of the voltage-to-current converters 2, 4, 5 are desirably summed, and drawn as an added constant signal to the variable pH signal, leaving the respective pS⁼ and temperature data lines to carry only the less sensitive pS⁼ and temperature signals which would be more prone to error from an additive constant signal introduction.

In order to avoid bidirectional current signals which could otherwise occur on current conversion of the voltage signal from the pH electrode (which normally would have a maximum output range of about 0 volts ±7 times its maximum 59.2 millivolt per pH unit sensitivity slope at 25° C.) a constant voltage is added to the pH line in excess of the maximum negative voltage which would be produced in the pH electrode signal. In the illustrated embodiment, the add-on voltage to the pH voltage signal is 1000 millivolts (1 volt) which is provided by voltage reference circuit 1, which draws constant current input from the pH line to desired voltage reference levels and establishes transmitter common voltage reference lines. In this connection, a one volt regulated source $V_2$ is established across resistor R11 of circuit 1, and an artificial common is established at the junction of resistors R12 and R15 such that a voltage $V_1$ of 1.0 volts in established between the common and a system common as shown in circuit 1. The constant reference voltages are utilized by the constant-current drawing voltage-to-current converters 2, 4, 5.

Subcircuit 2a of the temperature current converter circuit 2 converts voltage $V_2$ from the voltage reference circuit 1 into a constant current of 1 milliampere, which is directed through the resistance wire coil of the temperature probe sensor.

This voltage to current conversion of circuit 2a is accomplished by operational amplifier U2, pins 3, 4, 11, transistors Q10, Q15 and resistor 405, with the 1 ma current being supplied at the output of transistor Q10 which is forced to travel through the common 402 to which the temperature circuit is referenced, to the other side of the platinum coil temperature probe, to provide a voltage proportional to the temperature as determined by its temperature-resistance variation. The resulting voltage difference is utilized as an input into voltage current converter circuit 2b, comprising operational amplifier U2, pins 5, 6, 9, transistors Q11, Q12, and resistors R21, R22. Circuit 2a is thus seen to be a circuit which draws a constant current, and the circuit 2b output is a current signal representative of the temperature voltage information from the sensor 28. The resulting variable temperature output current signal drawn by circuit 2b via conductor 404 from pin 1 of terminal block (TB) 1 which connects to the temperature line of cable 18 through filter circuit 3a.

The voltage-to-current converter circuit 2b draws approximately 25 nanoamperes of current in the conversion of voltage to the current signal. However, it is undesirable to force even such a small amount of current through the pH or pS= ion selective electrodes and accordingly, circuits 4 and 5, which are high impedance voltage-to-current circuits, are provided which utilize very small amounts of currents from the electrode voltage source (on the order of about 10 picoamperes) and which each also draw substantially constant current from the voltage regulation circuit 1 in their operation. Circuit 4 comprises a partially integrated and partially discrete high impedance operational amplifier circuit which draws effectively constant current, and is connected as a voltage-to-current converting circuit associated with the pH electrode 22. Viewing pin 3 of Q6 as the noninverting (+) input, pin 7 of Q6 as the inverting (−) input, and pin 11 of U1 as the output of the partially integrated and partially discrete operational amplifier, circuit 4 is seen to be identical in function to circuit 2b in that it provides a current signal (through Q2 and Q3) representative of the voltage present at the noninverting operational amplifier input, which in this case is the voltage output of the pH sensor, plus V1. The variable current pH signal drawn by the transistor pair Q2, Q3 at conductor 406 is added to constant currents drawn by the transmitter circuitry along conductor 408, and the resulting constant and pH variable current is drawn from the controller unit along the pH line of cable 18, through pin 2 of TB1 and rf filter 3c.

Resistor R25 along with the capacitor C7 for a radio frequency filter circuit 6 for the high impedance pH input to circuit 4, which is adapted to remove rf signals which might otherwise be picked up on the pH electrode line.

The voltage potential utilized as the input for the pH voltage-to-current conversion in circuit 4 is the potential developed between the actual electrochemical input voltage from the pH electrode and the potential of system common bus 410 of voltage reference circuit 1, which is at a voltage V1 with respect to the artificial common line 401 of circuit 1.

In this regard, the reference electrode 24 is connected through pin 5 of TB1 to reference electrode input circuit 8 at voltage V1 with respect to system common bus 410. The common bus 410 may be traced through voltage reference V1 (through resistors R16 and R15 of circuit 1) to pin 13 of operational amplifier U1 of circuit 8 which is maintained at the same potential as pin 12 of U1 in voltage. Pin 12 of U1 is also the reference electrode connection which is thus at a base voltage V1. By connecting the reference electrode at a voltage V1 above the common bus 410, a voltage V1 is added to the pH voltage. Thus, if the pH of a solution is, for example, pH7, then by the addition of voltage V1 to the reference electrode potential, the resulting pH input to circuit 4 would be also at V1, because by definition of the pH electrode reference system, the voltage between the standard chloride reference electrode 24 and pH electrode 22 at pH7 is zero. In this manner, 1000 mv is added to pH signal, thus allowing the variable pH current to be unidirectional upon conversion to current representation by circuit 4.

Circuit 5 is the voltage-to-current converter for the sulfide electrode potential and is substantially identical to circuit 4. Like circuit 4 it provides a high impedance input of at least about $1 \times 10^{12}$ ohms for its associated electrode so that a current of about 10 picoamperes or less is permitted to flow through the electrodes. In circuit 5, the signal output current drawn by the collectors of transistors Q4 and Q5 is drawn directly from the controller 14 through the sulfide signal line of cable 18 to pin 3 of TB1, and through rf filter circuit 3b. This is distinguished from circuit 4 for the pH voltage current converter where the current is connected to a common bus 408 which receives a plurality of small, constant currents from the various parts of the transmitter circuitry which require power, as previously discussed. Circuit 9 is a means for providing a constant bias current out of the sources of Q6 and Q7 for circuits 4 and 5. Thus, the pH signal current which is drawn by the collector of transistors Q2 and Q3 of circuit 4 is combined with the other constant currents. The respective return (opposite) currents including the constant currents and the signal variable currents for the pH, temperature, and pS= signals, are collected at system common 410 and carried through protective and bias diodes CR3, CR4, through rf filter circuit 3d to pin 4 of TB1 for the common return line of the cable 18 to the controller. In this manner, the sulfide and temperature signal lines of cable 18 are provided with variable currents which only represent the respective sulfide and temperature information. In the case of the pH signal line, the constant currents used in the operation of the transmitter are added to the pH variable current signal, because the pH signal has a larger current sensitivity than the pS= and temperature signals.

Circuit 8 provides a conductive path for ac and dc leakage currents (from the controller, remote ground potential difference, auxiliary recorders, etc.) which could otherwise be forced through the electrodes with deleterious effects on accuracy and stability. In this regard, as previously discussed, pins 13 and 12 of U1 of circuit 8 are kept at the same potential when this operational amplifier is in normal operation, and accordingly, the reference electrode connection (pin 5 of TB1) is maintained such that it is at the same potential of the junction of resistors R12 and R15 (V1 one volt-above the transmitter system common bus 410). A low impedance current path is established to the grounded mud solution via ground pin bearing the voltage across transistor Q17 of circuit 8 such that the potential of the whole transmitter floats with respect to the ground pin until the reference electrode finds itself at a potential 1 volt above the transmitter common. Any leakage current will thus preferentially be conducted via the collector of transistor Q17 of circuit 8 to pin 6 of TB1 via the ground pin 28. The ground pin 28 is a low impedance electrode having an impedance of about 10 ohms or less (e.g. stainless steel pin) which is in direct electrical contact with the grounded mud. In the absence of this feature of circuit 8, the leakage current could be forced through the reference electrode to the mud. The reference electrode input impedance of circuit 8 is at least about 10 megohms.

Diodes CR4 and CR3 provide a voltage bias to keep the transmitter common bus 410 away from the absolute common line of cable 18 which goes to the control unit. This permits the various operational amplifiers of integrated circuits U1 and U2 to operate within their specifications in that the supply connections to the various operational amplifiers at pin 10 of U1 and pin 10 of U2 come directly off this absolute common 412. Thus, except for CR1 which is a protective diode to protect the transmitter in the event of reverse polarity hookup, the only connection to the absolute common 412 are these supply connections, and the emitter of transistor Q17 of circuit 8, the collector of which is connected directly to the solution ground. The voltage between the emitter and the collector of Q17 of circuit 8 is controlled by the operational amplifier U1 pins 12, 13 and 2 of circuit 8 to make the reference electrode base potential 1 volt above the transmitter common bus 410. Thus changes in the potential of the low impedance grounding electrode due to leakage currents flowing through it are absorbed by the transmitter, and by providing high impedance input circuits for the electrodes, the leakage currents are prevented from being forced through the delicate electrode membranes.

As indicated, these respective signal currents are drawn to the transmitter 14 from the controller 16 over the three signals wires of cable 18 (and return via the common return line of cable 18). The signal information is processed in the controller 16 to provide the compensated pH, pHS$^-$ and HP signals as discussed in connection with the schematic diagram of FIG. 3. The manner in which these output signals are obtained will now be generally discussed, and the specific circuitry of the embodiment of controller 16 for obtaining these desired signals will subsequently be discussed with reference to the circuit diagrams of FIGS. 5 and 6.

The sulfur content in drilling muds exists primarily in the following five states: (1) $H_2S$ (dissolved); (2) $HS^-$ hydrosulfide ion; (3) $S^=$ sulfide ion; (4) free sulfur(s); and (5) heavy metal sulfide precipitates. Sulfur in states 4 and 5 is normally not of immediate concern from the standpoint of safety, although it is possible to convert sulfur in states 4 and 5 to states 1, 2 and/or 3, under redox conditions or if the mud becomes acidic. However, drilling muds are generally maintained at a basic pH in the range of from about 8 to about 12 to provide various properties unrelated to sulfide control. The total soluble sulfur content of the drilling mud ($S_T$) may be defined as: $S_T = H_2S(\text{dissolved}) + HS^- + S^=$ The specific proportions of each of the three states relative to $S_T$ is dependent on the pH of the mud as shown in FIG. 2 of the drawings from which it may be seen that the soluble sulfur content of the mud is interchangeable between states 1, 2, and 3 with changes of pH of the mud. However, it will be appreciated from FIG. 2 that between pH 8 and 12, nearly all of the total soluble sulfur ($S_T$) exists as hydrosulfide ion $HS^-$. Accordingly, the total soluble sulfur content ($S_T$) of the mud in most drilling applications is almost equal to the $HS^-$ concentration. Thus, from a determination of $HS^-$ concentration, it is possible to determine how much sulfide scavenger should be added to precipitate out the sulfides that are likely to become an $H_2S$ hazard. It will also be seen that as the pH of the mud is decreased, the amount of dissolved $H_2S$, which would be available to establish an equilibrium with an $H_2S$ gas concentration in the ambient temperature, will increase, thus increasing the potential atmospheric $H_2S$ hazard.

Accordingly, the instrument 10 provides a compensated measurement of atmospheric hazard potential and $HS^-$ concentration through appropriate signal processing of the electrochemical potential measurement available from the pH, $pS^=$ and reference electrodes 22, 24, 26. The electrochemical potential $E_{pH}$ of the pH electrode with respect to a reference electrode may be expressed as a conventional Nernst equation:

$$E_{pH} - E_{ref} = E°_{pH} + \frac{RT}{2F}(\text{Log}_e [H^+]^2) + K \tag{1}$$

where K represents reference electrode Nernst expression $$-\left[E°_{ref} + \frac{RT}{nF} \log_e (\text{reference electrode species})\right]$$

Similarly, the electrochemical potential $E_{S=}$ of the sulfide electrode with respect to the reference electrode may be represented in Nernst equation form:

$$E_S = -E_{ref} = E°_S = -\frac{RT}{2F}(\text{Log}_e[S^=]) + K \tag{2}$$

Upon subtracting the Nernst sulfide potential of Equation 2 from the pH potential of Equation 1, a hazard potential $E_{HP}$ may be derived which is independent of reference electrode expressions, where $E_{HP} = E_{pH} - E_{S=}$, and $E°_{HP} = E°_{pH} - E°_{S=}$:

$$E_{HP} = E°_{HP} + \frac{RT}{2F}(\log_e [H^+]^2[S^=]) \tag{3}$$

The distribution of the various forms of soluble sulfur is a function of pH as discussed previously, and the soluble sulfur is also in potential equilibrium with the atmosphere. These equilibrium relationships may be represented by the following expressions:

$$K_1 = \frac{[HS^-]}{[H^+][S^=]} \tag{4}$$

$$K_2 = \frac{[H_2S] \text{ dissolved}}{[H^+][HS^-]} \tag{5}$$

$$K_3 = \frac{H_2S \text{ ppm}}{[H_2S] \text{ dissolved}} \tag{6}$$

where $K_1$ is the equilibrium constant between sulfide ion and hydrosulfide ion, where $K_2$ is the eqilibrium constant between hydrosulfide ion and dissolved $H_2S$, and where $K_3$ is the equilibrium constant between dissolved $H_2S$ and $H_2S$ gas in parts per million in the atmosphere (e.g., adjacent the mud). The following expression may therefore be obtained:

$$[H^+]^2[S^=] = \frac{H_2S \text{ ppm}}{K_1 K_2 K_3} \quad (7)$$

Appropriate substitution of Equation 7 for the $[H^+]^2[S^=]$ expression of Equation 3 provides the following expression:

$$E_{HP} = E°_{HP} + \frac{RT}{2F}\left(\text{Log}_e \frac{H_2S \text{ ppm}}{K_1 K_2 K_3}\right) \quad (8)$$

Because the standard electrochemical hazard potential $E°_{HP}$ is a constant, and because the log of the indicated constants $K_1$ $K_2$ $K_3$ is a constant, at constant temperature, Equation 7 may be re-written such that $E_{HP}$ is shown to be a direct function of the log of the potential equilibrium $H_2S$ gas concentration:

$$\text{Log}_e (\text{ppm } H_2S \text{ gas}) = (E_{HP} - E°'_{HP})\frac{2F}{RT} \quad (9)$$

where $E_{HP}°' = E_{HP}° + (RT/2F) \log_e (1/K_1 K_2 K_3)$. In this connection, values of the indicated constants are approximately as follows:

$K_1$, about $1 \times 10^7$
$K_2$, in the range of about $1 \times 10^{12}$ to $1 \times 10^{14}$
$K_3$, about $1 \times 10^7$
$E_{HP}°$, about 450 millivolts The appropriate derivation of the HP signal is provided by the control unit 16.

In connection with derivation of the $HS^-$ concentration signal, half of the pH-reference potential may be subtracted from the sulfide reference potential; thus, subtracting half of Equation (1) from Equation (2) produces the following expression:

$$E_S = -E_{Ref} - \frac{1}{2}(E_{pH} - E_{Ref}) = (E°_S = -\frac{1}{2}E°_{pH}) \underline{\quad}^{(10)}$$

$$\frac{RT}{2F} \log_e([H^+][S^=]) + \frac{K}{2}$$

Because $$[H^+][S^=] = \frac{[HS^-]}{K_1},$$

Equation (10) may be re-written as $$(E_S = -E_{ref}) - \frac{1}{2}(E_{pH} - E_{ref}) = \quad (11)$$

$$\left[(E°_S = -\frac{1}{2}E°_{pH}) - \frac{RT}{2F} \log_e \frac{1}{K_1}\right] -$$

$$\frac{RT}{2F} \log_e [HS^-] + \frac{K}{2}$$

Therefore, by electronically subtracting half of the pH signal from the sulfide signal, the resulting signal is directly proportional to $pHS^-$, since at constant temperature $E_S° =, E_{pH}°, K_1$ and K are essentially constant.

Thus, $-\log [HS^-]$, which by definition is $pHS^-$, may be derived from the measured potential of the sulfide-reference electrode system and the pH-reference electrode system.

It will be appreciated that the measured potential of the electrochemical systems will vary with the temperature of the drilling mud. The measured values for pH and the derived values for $pHS^-$ and HP should accordingly be temperature-compensated. Furthermore, individual electrodes, and particularly pH electrodes, may have a response sensitivity which deviates from the ideal sensitivity, generally by having a diminished output voltage vs. log concentration response slope. Thus, while pH electrode sensitivity slope may ideally be 59.2 millivolts/concentration decade, individual electrodes may vary from, say, 48 millivolts per decade of species concentration, to 59.2 volts per decade, and circuit means for compensating for such electrode sensitivity variation should desirably be provided.

In connection with pH electrode temperature compensation, the electrode potential output variation with temperature may be compensated by normalizing the electrode response curve about its isopotential point, a point on the electrochemical potential vs. $H^+$ concentration curve at which there is no substantial variation in potential with temperature. The isopotential point for a pH electrode will generally be at a pH of 7 in an aqeuous system such that a family of output potential versus concentration function response curves representative of operation at different termperature will all pass through the isopotential point at pH 7. Because the response curves of the output potential are generally linear functions when the species concentration function is a log function, the temperature compensation may be accomplished by adjusting the slope of the linear functions to normalize the slope to that for a predetermined, standard temperature. The slope may readily be adjusted by adjusting the gain of an amplifier such as an operational amplifier (in a voltage gain configuration) in which the linear potential vs. log $[H^+]$ concentration function is biased with the isopotential output voltage and with the isopotential species concentration, respectively. In this manner, the isopotential point may be thought of as being displaced to the origin of voltage and concentration coordinates, so that the slope of the linear function may be normalized simply by a temperature-compensatory change in the gain of the amplifier. Individual variations in electrode sensitivity may be compensated to a predetermined response sensitivity by gain variation at the isopotential point normalized response curve. The isopotential point normalizing bias(es) may be restored after temperature and/or sensitivity compensation.

It has been determined that the hazard potential function and the $pHS^-$ function previously discussed have respective isopotential points at which the functions of system potential do not change with changing temperature. These points may be determined by differentiating the respective functions with respect to temperature to determine the point at which the rate of change with respect to temperature is equal to zero. Thus, by normalizing the species response functions to their respective isopotential points, temperature (and sensitivity) compensation may readily be made by adjusting of amplifier gain. The normalizing bias values may be restored after compensation.

As indicated, such compensation may be applied through the use of an operational amplifier in a voltage gain configuration, in which the gain is determined by the ratio of the resistance $R_f$ of a resistance connection between an amplifier input (e.g. the inverting input) and output channels, and the resistance $R_{in}$ of a voltage signal to the input channel. By digitizing the $R_f$ and/or $R_{in}$ restance values through the use of appropriately controlled fixed resistor elements and switches, the gain function may be made a discrete function which is correlatively responsive to discrete temperature or electrode sensitivity information. As will be further described in connection with the specific circuitry of the controller, such digitized, isopotential gain circuits are utilized in the provision of effective and efficient instrumentation circuitry in accordance with the present invention.

Figure 5:
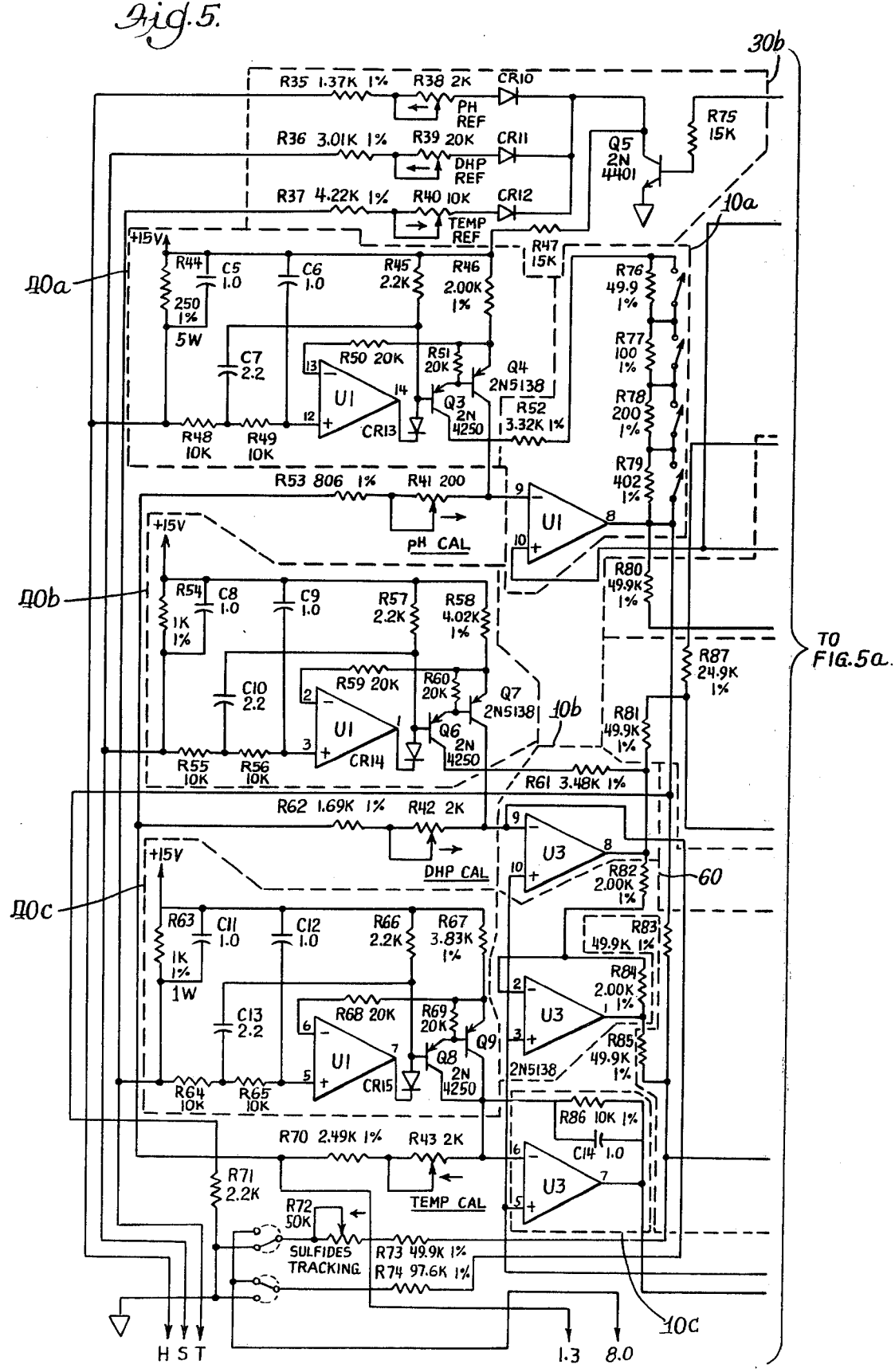
FIGS. 5, 5a, and 6 and 6a, are circuit diagrams of the control board of the control instrument of the apparatus of FIG. 1.
Figure 5A:
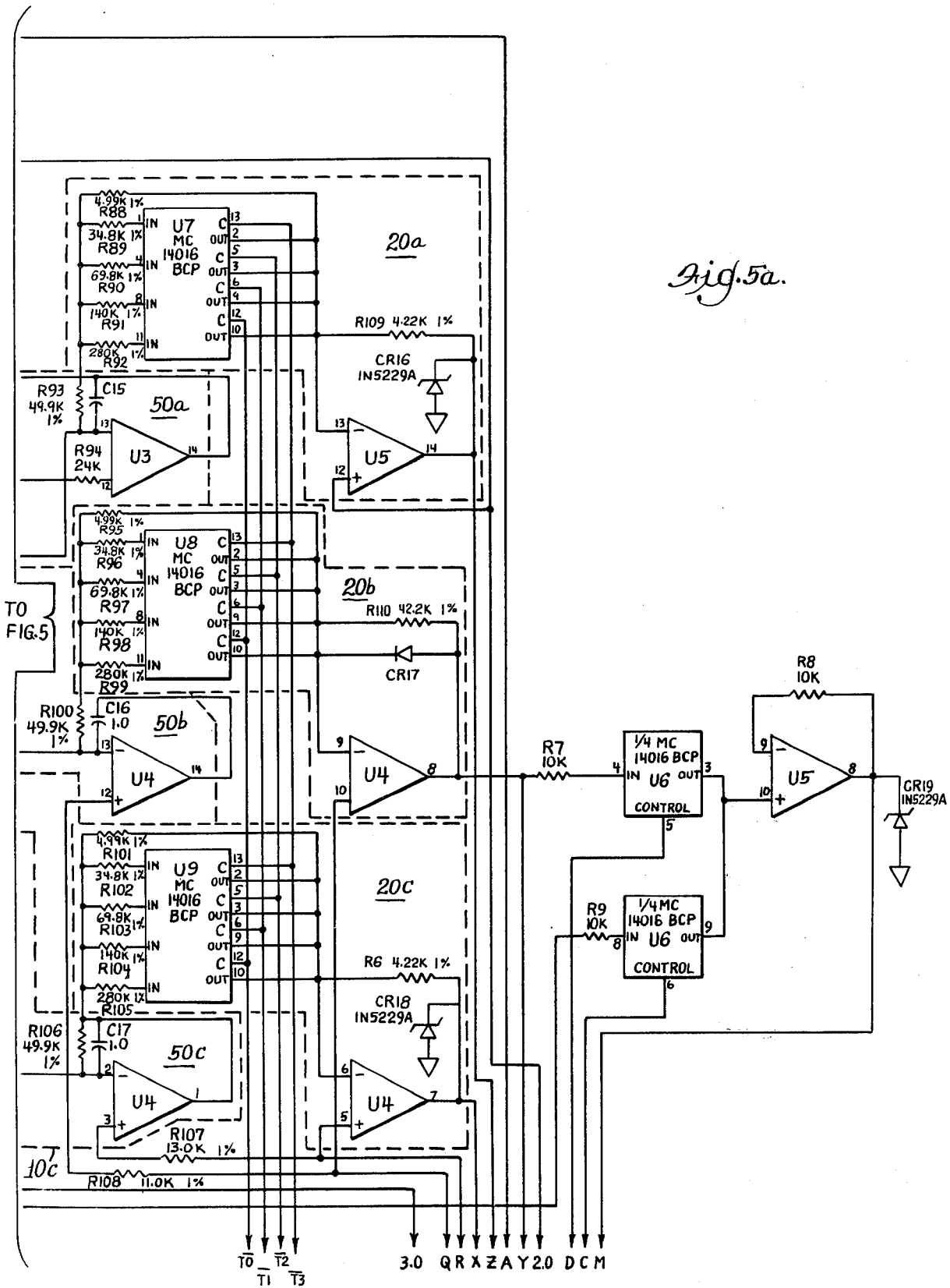
Figure 6:
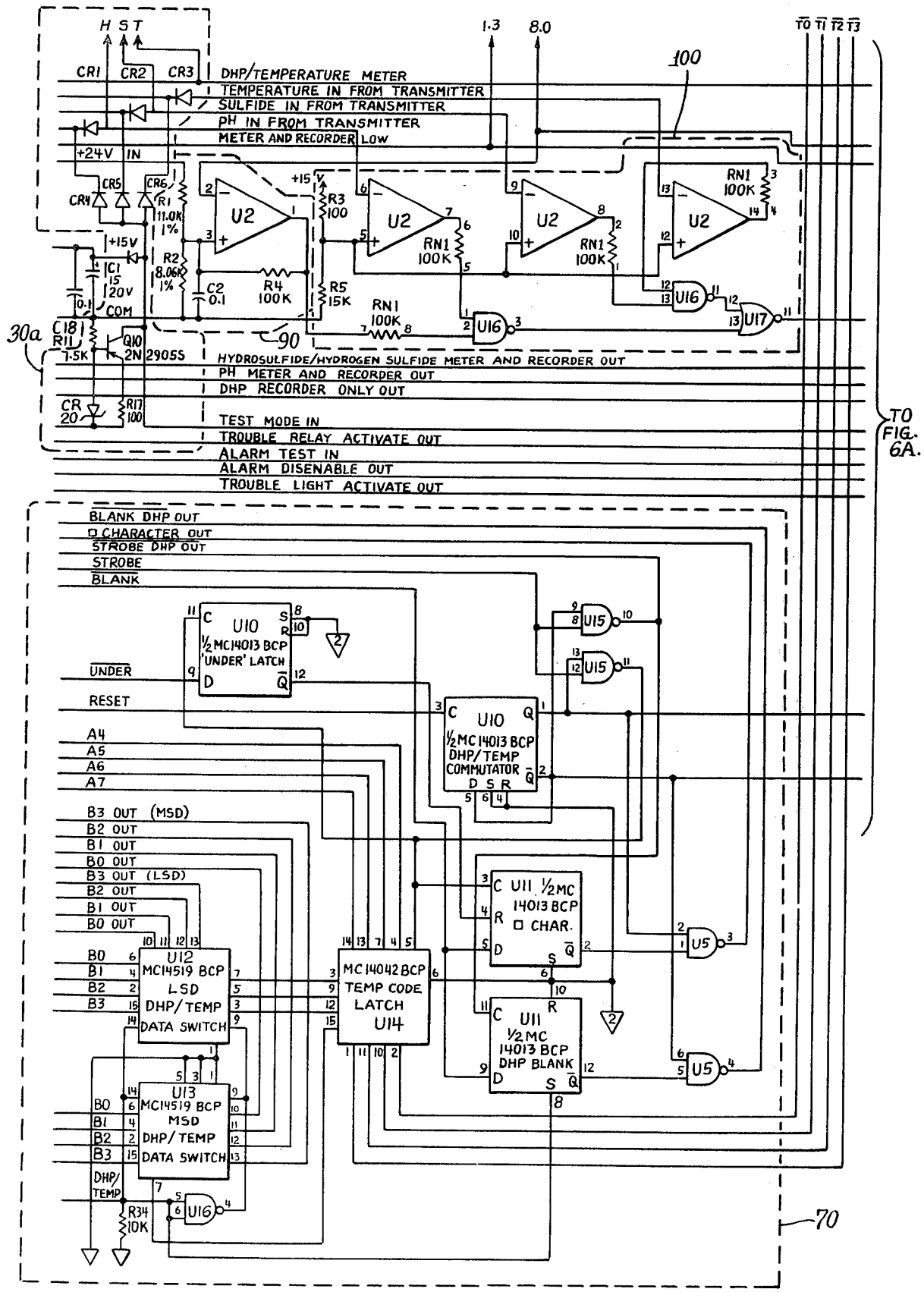
Figure 6A:
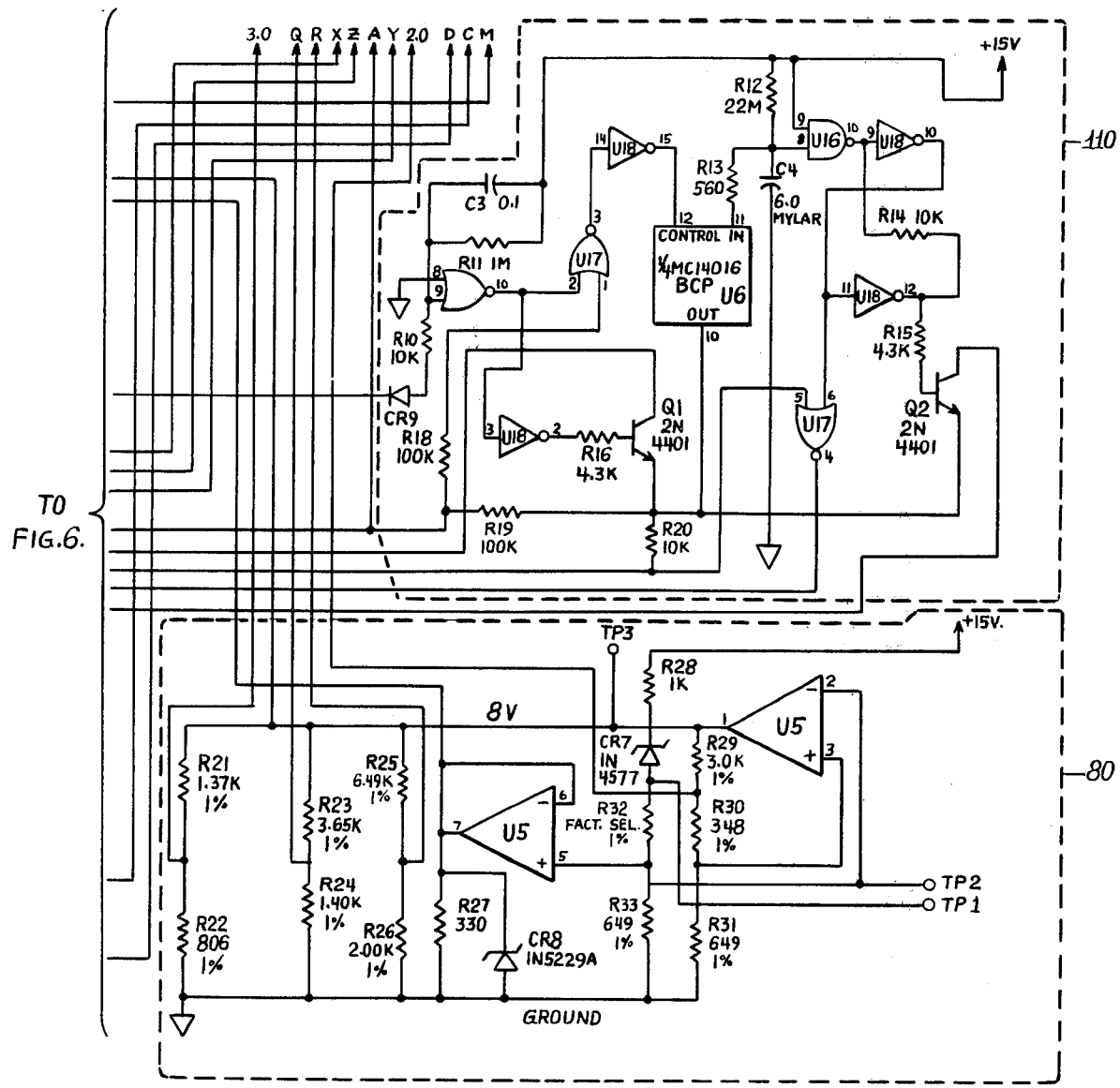

Turning now to FIGS. 5, 5a, and 6, and 6a arithmetic circuits 342 (FIG. 3) which process and compensate the signal currents and circuits generally related to the arithmetic circuits will now be more specifically described. The illustrated circuit diagram has been separated into the 4 sheets of drawing, FIGS. 5, 5a, 6, 6a such that FIG. 5 is the upper left hand corner of the circuit, FIG. 5a is the upper right hand corner of the circuit, FIG. 6 is the lower left hand corner of the circuit, and FIG. 6a is the lower right hand corner of the circuit. The circuit of FIGS. 5, 5a, 6, 6a should be considered to be one continuous circuit joined at the respective connections bearing the matching letter or voltage reference designations, hereinafter, in this specification reference to FIG. 5 will include FIGS. 5 and 5a, while reference to FIG. 6 will include reference to FIGS. 6 and 6a.

The circuitry of FIGS. 5 and 6 comprises digitized operational voltage amplifier circuit means 10 for compensating (standardizing) the response sensitivity of an isopotential normalized pH electrode signal, and circuit means 20a, b, c for temperature compensation of respective isopotentially normalized pH, pHS⁻ and pHP [i.e. log (hazard potential)] signals, and further comprises circuit means 30a, b for providing reference signals (see test controls 328,324 of FIG. 3). The circuitry also includes a plurality of translator filter means circuits 40a, b, c for converting the respective current signals drawn through the pH, pS=, and temperature lines of cable 18, to voltage representation, and for filtering any audio frequency components on the lines.

In normal operation, the three data signal lines for pH, pS= and temperature current signals drawn to the transmitter are connected to pins 8, J and 9 on the edge connector 500 of the control board circuit as shown in FIGS. 5 and 6. These signals go to the respective lines of cable 18 to the transmitter through intermediate connection through respective radio frequency filters on the mother board (not shown) identical to filter circuits 3a, b, c, d of the transmitter circuitry. In this mode, diodes CR1, CR2 and CR3 of circuit 30a are biased in the forward direction because the current is flowing from a 15 volt supply through respective current sensing resistor R44 of pH input circuit 40a, current sensing resistor R54 of pS= input circuit 40b, and current sensing resistor R63 of temperature input circuit 40c, out to the transmitter. If the pH, pS= or temperature of the mud increases (or decreases) the current increases out to the transmitter on the respective signal line, and the voltage drop across the respective sensing resistor increases (or decreases). In this manner, the signal information from the transmitter electrodes and sensor is supplied to the controller circuitry. However, when the front panel test switch is depressed, the instrument goes into a test mode in which an artificial test set of pH⁺, pS= and temperature signals supplied by circuit 30b is substituted for the actual signals.

Operational amplifier circuit means 50 a,b,c are respectively provided in connection with the temperature compensation circuits 20 a,b,c for inverting and filtering the respective pH, pHP and pHS⁻ signals, and circuit means 60 is provided for pHS⁻ signal derivation.

The control circuit further comprises logic circuit means 70 for commutating the A/D conversion of the temperature and pHP signals, reference circuit means 80 for providing voltage reference potential, voltage comparator circuit means 90 (detector 388, FIG. 3), circuit means 100 for low current detection (detector 361, FIG. 3), and circuit means 110 for detecting circuit failure (see delay circuit 396, FIG. 3).

When the instrument is in the test mode, the transmitter currents are pulled directly to the 15 volt supply without going through current sensing resistors R44, R54, and R63, and protective diodes CR1, CR2, CR3, CR4, CR5, CR6 are provided to prevent instrument damage from shorting in either the test mode or the operational mode. In the test mode, the current through the current sensing resistors R44, R54 and R63 is controllable by variable resistors R38, R39 and R40 of circuit 30b rather than by the information signal current to the transmitter, so that the instrument may be tested to see if it is working normally (e.g. by setting the pH and pS= values and checking the corrections of the HP value derived by the instrument).

However, the arithmetic circuitry of the control unit functions in the same manner whether there are actual signals from the transmitter or reference signals from circuit 30b applied to the input circuits 40a,b,c.

In any event, the current signals from the transmitter or test circuit 30b are transferred into voltage signals by the current sensing resistors R44, R54, R63, in translator filter circuits 40a,b,c. Circuit 40a is a translator filter circuit for the pH signal, circuit 40b is a translator filter circuit for the pS= signal, and circuit 40c is a translator filter circuit for the temperature signal. These substantially identical circuits also filter the input signal to further remove spurious high frequency signals. The filtered voltage signals are subsequently retransformed to current signals by the circuits 40a,b,c.

The translator filters 40a,b,c are primarily adapted for the removal of undesired lower frequencies in the range of, for example about 10 hz to about 1 Mhz, with higher frequencies being removed primarily by rf filters such as filters 3a, 3b, 3c, 3d.

In pH translator filter circuit 40a, the filtered pH voltage signal developed across resistor R44 is input to operational amplifier U1 pins 12, 13, and is output as a current signal at the collectors of Q3 and Q4. Accordingly, the input to circuit 10a comprises two currents, one of which is the current-to-voltage-to-current pH current signal, and the other of which is a current controlled by resistors R53 and R41, which is a constant current adjustable from the front panel (corresponding to pH cal pot 326, FIGS. 1, 3). Through the use of this variable resistor R41, the amount of constant current subtracted from the current coming in from the translator filter circuit for the pH signal may be varied for calibration solution of known pH. The amount of current subtracted includes an amount of current to compensate for the constant current transmitted over the pH line for utilization by the transmitter constant current circuit elements. Circuits 40b and 40c function in substantially the same way as circuit 40a to perform a translation-filtering function on the pS= and temperature signals, respectively. The pS= calibration for the output signal from transistors Q6 and Q7 of circuit 40b is performed by variable resistor R42, and the temperature signal calibration for the output current signal of transistors Q8 and Q9 of circuit 40c is similarly provided by variable resistor R43. It will be appreciated that in the illustrated embodiment there is no constant current signal to the transmitter which should be removed by circuits 40b and 40c.

As previously discussed, the isopotential point of the pH signal is made to correspond to zero signal through the pH signal amplifier circuitry so that adjustments may readily and directly be made to the gain of the pH signal to compensate the slope of the pH electrode without affecting the isopotential at pH 7. Accordingly, the operating point of pH amplifiers U1 pins 8, 9, 10 of electrode sensitivity compensating circuit 10, U3 pins 12, 13, 14 of inverting filter circuit 5a and U5 pins 12, 13, 14 of digital temperature compensating circuit 2a are set to a potential 0.7 volts above the 1.3 volt pseudo ground. Thus, pin 10 of pH amplifier U1, pin 12 of pH amplifier U3, and pin 12 of pH amplifier U5 are all set at 2.0 volts.

Circuit 10a is the sensitivity compensation circuit for the pH electrode response, and comprises a plurality of binary valued resistors R76, R77, R78, R79 in the feedback resistance circuit further including resistor R52 between pins 8 and 9 of operational amplifier U1. Thus, resistor R76 has a resistance value twice that of R77, which in turn is twice that of R78, which is twice that of R79. The resistance value of each of the resistors R76-79 may be added to the feedback resistance $R_f$ by corresponding switches associated therewith in a manner to change the gain of circuit 10a over a range divided which may be divided into 16 discrete intervals by appropriate manipulation of the resistor switches.

In the illustrated embodiment the various resistance values are selected to provide for gain compensation in circuit 10a for pH electrodes having sensitivities in the range of 48 millivolts/decade to 60 millivolts/decade, to provide the electrode with a nominal sensitivity of 60 millivolts/decade and to provide a gain such that the output of circuit 10a is 100 millivolts per decade at 25° C. The switches of circuit 10a may be made inaccessible from the front panel to reduce the opportunity for undesired adjustment. The switches may be readjusted upon electrode replacement, and replacement electrodes may be pre-tested and supplied with switch settings appropriate to correct for their individual deviations from ideal sensitivity.

The pH signal output at amplifier U1 pin 8 of circuit 10 increases with increasing pH, and is supplied to pH filter circuit 50a for filtering and inversion.

The amplifier stage 50a (and correspond circuits 50b, c) has a unity gain and is primarily utilized to provide signal inversion so the signal will be at proper polarity for input to the pH temperature compensation circuit 20a.

However, while amplifier filter stages 50b and 50c are similar to amplifier stage 50a, these stages are also utilized to appropriately combine the pH and pS= signals to provide the pHP and the pHS−0 signals, respectively.

Thus, the pS= signal output from translation filter 40b is directed to an amplifier stage 10b which applies a gain such the pS= output signal at U3, pin 8 has a slope of 100 millivolts per decade of sulfide ion concentration at 25° C. when a sulfide sensor having a sensitivity of 29.6 mV/decade is used. In the illustrated embodiment, the gain of circuit 10b is not programmable like that of circuit 10a for the pH electrode because the pS= electrode has a near-thoretical slope response of 29.6 millivolts per concentration decade. However, it will be appreciated that increased accuracy could readily be provided through the addition of a digital gain programming feature to circuit 10b like that of circuit 10a.

As indicated, the pH and pS= signals are appropriately combined in circuit 50b, c and for convenience in this regard, inverting operational amplifier circuit 60 is provided for inverting the pS= signal from U3, pin 8 of circuit 10b. The inverted $pS^E$ = signal is provided at U3 pin 1 of circuit 60. Accordingly, the pH signal is provided in one polarity at amplifier U1 pin 8 of circuit 10a, and in the other polarity at amplifier U3 pin 14 of circuit 50a. Similarly, the pS= signal is provided in one polarity at amplifier U3 pin 8 of circuit 10b, and in the opposite polarity at amplifier U3 pin 1 of circuit 60. Note that the pH signal slope (formerly nominally 60 millivolts/decade) is now equal to the pS= slope (formerly nominally 30 millivolts per decade), so that in combinations, the pH signal must be treated as one half the actual signal.

To provide the pHP signal, the pH signal polarity available from U3 pin 14 and the pS= signal polarity available from U3 pin 8 are added to the summing node at amplifier U4, pin 13 of circuit 50b. However, because the pH is twice as influential in determining the pHP signal as the pS= signal, these signals are input through different input resistors R87 (for pH) and R81 (for pS=) where R87 is half the resistance of R81 so that the halved pH signal has twice as much gain in circuit 50b as the pS= signal, so the signals are combined on an equal basis. Output 50b provides an output signal of 100 mV/decade.

The HP amplifier circuit is operational at the isopotential point of the resulting pHP signal, and accordingly, the amplifier U4 pins 12, 13, 14 is set to operate at an isopotential point which corresponds to about 0.02 parts per million of $H_2S$, a value calculated from the best presently available experimental and theoretical data.

Because the HP meter circuitry operates at a zero reference point of 1.3 volts like the pH meter circuitry, and because it further has a signal response conversion of one volt per decade, the isopotential point of about 0.02 ppm for the HP amplifier circuitry is about −1.614 volts or −0.314 volts absolute. Since the amplifier cannot be made to operate around −0.314 volts due to system power supplies being only positive, an arbitrary operating point of 2.2 volts is used for amplifiers U4 pins 12, 13, 14, and U4 pins 8, 9, 10. A constant current through resistor R74 is provided which is adapted to cause the output of the amplifier in circuit 20a to attempt to be about −0.314 volts at 2.2 volts input, making 2.2 volts the effective isopotential point. (The gain can be changed without affecting the output when the input =2.2 V). The amplifier in circuit 20a is not operating normally at 0.02 ppm but it achieves normal operation when the output is between 0-99 ppm (1.3-3.3 volts).

The pHS− signal is derived in a similar manner at circuit 50c. In this regard, the pS= signal of polarity from amplifier U3 pin 1 routed through resistor R85 to the summing mode of circuit 50c at operational amplifier U4, pin 2. The pH signal of polarity from amplifier U1 pin 8 is similarly routed through input resistor R83 to U4, pin 2 of circuit 50c, with R83 having the same value as R85 because the pH and pS= signals are combined in the same proportions in circuit 50c. The pHS− circuit operational amplifier circuitry is also operated at the isopotential point of the pHS− system which is at about pHS− of 5.9 similarly based on best presently available experimental and theoretical data. This corresponds to a voltage of about 1.89 in operational amplifier circuit U4, pins 1, 2, 3, which includes constant voltages from the electrode system, and constant voltages introduced by the circuitry such as the 1.3 volt meter reference ground previously discussed. It should also be noted that like the circuit 50a, inverting filter stages 50b, c also have a filter network to provide a filter stage for undesired audio frequency signal components.

From the respective circuits 50a, b, c, the pH, pHP and pHS− signals are conducted to respective isopotential, temperature compensation stages 20a, 20b, 20c, which have digitally controlled, discrete gain variation responsive to digital temperature information, for compensation of the variation of the signals with temperature. In this regard, it will be recalled that in pH slope standardization circuit 10a, four binary value resistors R76, R77, R78, R79 are provided to digitally adjust the feedback resistance $v_f$ of differential amplifier U1, pins 8, 9, 10 over 16 steps of pH gain which are correspondingly selectable by four switches adapted to enable or disenable the four resistors. Each resistor in the R76-R79 series is twice the value of the preceding resistor and the values of those resistors may be varied in combination with the value of feedback resistor R52, to provide for the gain range in respect of the pH electrode compensation.

Temperature compensation circuits 20a, b, c, similarly comprise a network of fixed resistors and switches, the operation of which will be specifically described with respect to circuit 20a. Circuit 20a comprises operational amplifiers U5, pins 12, 13, 14 in inverting voltage gain configuration with a feedback resistance $R_f$ determined by fixed feedback resistor R88 and switchable binary value resistors R89, R90, R91, R92. This produces an operational amplifier circuit adapted to provide a digitally controlled gain range. The binary resistors R89-R92 are controlled by the temperature information derived from the transmitter which is digitized and stored by binary A/D converter 356 and temperature data latch 376 (FIG. 3). The resistor switching is controlled by integrated circuit switch U7, pins 1, 4, 8, 11 (input) 2, 3, 9, 10 (output) 13, 5, 6, 12 (control) of circuit 20a as shown in FIG. 5. The binary data is supplied to the control pins 13, 5, 6, 12 of U7 to enable or disenable resistors in corresponding binary value relationships, to effect incremental gain variation such that the output signal at U5, pin 14 does not vary with temperature. Of course, the pH amplifier U5, pins 12, 13, 14 is operated at the pH isopotential point of the circuit of 2 volts (pH isopotential point of 0.07 volts plus 1.3 volt instrument ground). Thus, the amplifier U5, pins 12, 13, 14 compensates for the variations in pH slope with temperature. The gain range provided by circuit 20a (and 20b, c) is correlated to the temperature range of the drilling mud, and in this regard the circuits 20a, b, c are adapted to operate over a temperature range extending from zero to 80 degrees C. (drilling mud will not normally exceed about 65° C.). Thus, each digitized division of the circuits 20a, b, c corresponds to 5° centigrade.

The pHP temperature compensation circuit 20b is substantially identical to pH circuit 20a, except that it is operated at 2.2 volts rather than the pH isopotential point, and is provided with a different fixed resistance value R110 to provide a 1 volt per decade HP signal.

The pHS− temperature compensation circuit is like that of circuit 20a, and is operated at the pHS isopotential point as discussed in connection with circuit 50c.

Thus, temperature compensated pH, pHP and pHS− signals are provided at the respective outputs of circuits 20a, b, c. From pin 14 of amplifier U5 of circuit 20a, the pH signal is routed directly off the board via edge connection to the pH analog to digital signal convertor 346 and display 318 as shown in FIG. 3. The pHS− signal is similarly routed from pin 7 of amplifier U4 of circuit 20c to A/D converter 350 and display 302. The compensated pHP signal from amplifier U4, pin 8 of circuit 20b is commutated to A/D converter 356 for antilog conversion and eventual display at display 308.

As indicated, digitized temperature information is used in circuits 20a, b, c and in this regard, analog temperature signal from the temperature translator filter 40c is directed to the summing node at pin 6 of amplifier U3, pins 5, 6, 7 where temperature calibration variable resistor R43 (calibration control 326 of FIG. 3) enables the removal of a constant from the temperature signal current input to calibrate the output at pin 7 of amplifier U3, pins 5, 6, 7 to the desired temperature reading. The temperature signal and the pHP signal are alternately directed to the A/D converter 356, and this commutation is carried out by a commutator circuit comprising integrated switches U6, pins 3, 4, 5 and pins 6, 8 and 9 together with operational amplifier U5 pins 8, 9 and 10. The two parts of integrated circuit U6 are similar to integrated switch circuits U7, U8 and U9 used in digital temperature compensation circuits 20a, b, c.

Switch U6, pins 3, 4, 5 controls the input of the pHP signal to amplifier U5, pins 8, 9, 10 from the output of circuit 20b, while switch U6, pins 6, 8, 9 controls the input of the temperature signal from pin 7 of amplifier U3, pins 5, 6, 7, to commutate the data into the data converter 326 (FIG. 3) so that the same A/D converter may be used for digital conversion of the respective pHP signal and temperature signal.

In operation, switch U6, pins 3, 4 and 5 and switch U6, pins 6, 8 and 9 alternately connect to operational amplifier U5, pin 10. When the control signal at pin 5 for switch U6 pins 3 and 4 is activated, that switch conducts the pHP output from circuit 20b into operational amplifier U5 configured as a unity gain voltage follower circuit having the same voltage at the input and the output. In this manner, the impedance of switches U6, pins 3, 4, 5, 6, 8, 9 does not substantially affect the A/D conversion. Moreover, 10 K resistors R7, R9 isolate the outputs of temperature calibration circuit U3, pin 7 and the pHP circuit 20b to avoid noise in the circuit and to limit the amount of current which flows between the differing voltages appearing at the output of amplifier U4, pin 8 of circuit 20b and amplifier U4, pin 7 of circuit 20c.

As previously discussed in connection with FIG. 3, the digitally converted pHP information is routed through a read-only memory look-up table which converts it to a linear quantity for display.

The alternately selected output of commutator amplifier U5, pin 8 is directed to the A/D converter 356 along conductor M (to FIG. 6) under the control of logic circuit 70 (FIG. 6). Each time the A/D converter 356 goes through one conversion, it puts out a reset pulse which in addition to being used for internal A/D function, changes the state of the "flip-flop" circuit U10, pins 1, 2 and 3 of circuit 70.

The output of pins 1 and 2 of the flip-flop circuit U10 are directed respectively to switches U6, pins 3, 4 and 5 and U6 pins 6, 8 and 9 to effect the previously described alternating signal selection. Other circuitry appropriately correlates the A/D converter data output for transmission and storage at the HP data latch 358, or temperature data latch 376 (FIG. 3). This determination of data type is also based on the state of U10 pins 1 and 2. The analog input signals are switched just after to a strobe pulse (over strobe conductor of circuit 70) which strobe pulse transfers the data in the counters of the A/D converter 356 to latches U14 which store the information. The temperature latch information is transmitted to the temperature compensation circuits 20a, b, c by conductors T0, T1, T2, T3. The HP latch is physically located with the A/D converter 356 (FIG. 3) which performs the conversion.

It is determined through the output Q and Q of flip-flop U10, pins 1, 2 through nand gates U15, pins 8, 9, 10 and nand gate U15, pins 12, 13 and 11, whether the data will be strobed into the HP latches or temperature latches U14. The HP latch command leaves the control board to the HP latches via conductor entitled "not strobe HP out". Temperature strobe information is given to latch U14, pin 5 by nand gate U15, pin 11. Other data, such as indication of overrange or underrange data, is received by flip-flop U10, pin 12, flip-flop U11, pin 2 and flip-flop U11, pin 12. Lines A4-7 represent unlatched temperature data, and the lines B0-3 represent respectively latched HP data (in) and selected data for display (out) Logic circuit 70 also provides for display selection for the data through appropriate routing circuitry. In this regard, HP is normally displayed on the front panel, but by pressing the display light switch previously described, the temperature information will be displayed. This function is handled by integrated switch circuits U12 and U13 of circuit 70.

Circuit 80 of FIG. 6 is a voltage reference circuit similar to the voltage reference circuit 1 of the transmitter. It employs a reference zener diode CR7 through which is maintained a constant current by operational amplifier U5, pins 1, 2 3. A constant reference voltage supply is provided at operational amplifier U5, pin 1, with reference to the ground potential of the instrument. This circuit provides the low impedance 1.3 volt supply which is the artificial meter ground.

Diode CR8 is a protective diode similar to diodes CR16, 17, 18 provided in circuits 20a, b, c. These prevent the A/D converter inputs from exceeding 5 volts. Resistors R25, R26, R23, R24, R21 and R22, are voltage dividers off an 8 volt precision supply which provides the isopotential voltage points for use in the inverting gain operational amplifier circuits of FIG. 5.

Circuits 90 is voltage comparator circuit which runs off of a 24-28 volt supply, to compare that 24 volt supply against a reference to see of it has dropped too low (e.g., 19.5 volts) for normal operation of the apparatus 10.

Circuit 100 is a low current detector comprising the three operational amplifier sections of U2 which are three comparators for testing whether enough current is flowing through the current sensing resistors R44, R54 and R63, to indicate that the transmitter is in normal operation. If sufficient current is not flowing to indicate normal operation, circuit 100 will assume that an open circuit condition exists (e.g., one of the transmission wires of cable 18 has been broken) and will appropriately change logic states. The signals from all the U2 operational amplifiers of both circuit 9 and circuit 10 are all combined in one signal at nand gate elements U16, pins 1, 2, 3 and 11, 12, 13 and nor gate element U17, pins 11, 12, 13. The combined signal thus provided at nor gate U17, pin 1 is a combined "trouble" signal to circuit 110 which, after a slight time constant delay determined by capacitor C3 and resistor R10, will de-energize the trouble relay 390 and cause capacitor C4 to discharge quickly through resistor R13 and control switch U6, pins 10, 11 and 12. When capacitor C4 is discharged past the voltage threshold of control switch U16 at pin 8, then control switch U16, pin 10 will go high, U18, pin 10 will go low, U18, pin 12 will go high, which will energize transistor Q2 through R15 and cause the "trouble" light 325 to turn on at the instrument panel.

If the aberrant condition(s) returns to normal the original condition of circuit 110 will be restored after a time during which capacitor C4 is slowly charged through resistor R12.

The circuitry of FIGS. 4, 5 and 6 is shown in detail including specific components layout and circuit element values. Further in this regard, the indicated resistances are in ohms, and capacitances are in micro farads. The diodes are 1N4148 diodes of Fairchild Semiconductor, the operational amplifiers are LM324 integrated circuits of National Semiconductor, with supply connections as follows:

|  | V+ | COM |
|---|---|---|
| U1, U2 | +28V to pin 4 | pin 11 |
| U3, U4, U5 | +15V to pin 4 | pin 11 |

The indicated CMOS supply connections are as follows:

| Motorola CMOS part no. | V+Pin (15 volts) | COM Pin |
|---|---|---|
| 14016 (Analog SW) | 14 | 7 |
| 14013 (Flip-Flop) | 14 | 7 |
| 14011 (Nand) | 14 | 7 |
| 14001 (Nor) | 14 | 7 |
| 14042 (Latch) | 16 | 8 |
| 14519 (Data SW) | 16 | 8 |
| 14047 (Inverter) | 16, 1 | 8 |

The appropriate connectors are made to conventional circuit elements as shown in FIG. 3, which need not be further described.

Accordingly, it will be appreciated through the present disclosure, methods and apparatus for remotely monitoring soluble sulfides in demanding environments such as oil well drilling muds, have been provided. The instrument may be calibrated with a suitable reference solution, such as by means of a test kit comprising a container having therein a predetermined amount of buffering agent (e.g. 500 cc. of very pure 0.0666 molar borax solution) and a prepackaged, dry mixture of an $H_2S$ clathrate compound and an antioxidant (e.g. 4.4 grams of ascorbic acid and 0.05 grams of a stable $H_2S$ releasing primary gas standard clathrate product of Chromalytics Corporation, division of SPEX Industries, Inc.) When mixed, the antioxidant dissolves, and the clathrate releases its $H_2S$ to give a test solution of pH 9.3, HP 10, and pHS 3.2 is provided by the indicated materials. It will further be appreciated that while the present inventon has been particularly described with respect to one specific embodiment, various modifications and adaptations will be apparent based on the present disclosure, and such modifications and adaptations are intended to be within the spirit and scope of the present invention.

Various features of the invention are set forth in the following claims.

I claim:
1. Apparatus for determining the hydrogen sulfide gas concentration in gaseous equilibrium with a soluble sulfide containing well drilling mud, comprising, in combination,
   hydrogen ion electrode means for providing an output signal having an electrical potential which is a function of hydrogen ion concentration,
   sulfide ion electrode means for providing an output signal having an electrical potential which is a function of sulfide ion concentration,
   means for subtracting said signal representative of sulfide electrode potential from said signal representative of hydrogen ion electrode potential to provide a difference output signal which varies as a function of the gaseous hydrogen sulfide equilibrium concentration.

2. Apparatus in accordance with claim 1 further including means for combining a signal representative of a predetermined compensation potential value with said sulfide ion representative signal and said hydrogen ion representative signal such that said difference output signal is proportional to gaseous hydrogen sulfide equilibrium concentration.

3. Apparatus in accordance with claim 1 wherein said signal subtracting means produces a difference output signal which is a logarithmic function of the gaseous hydrogen sulfide equilibrium concentration of said mud substantially as follows:

$$\mathrm{Log}_e \text{ (ppm H}_2\text{S gas)} = (E_{HP} - E_{HP}^{o\prime}) \frac{2F}{RT}$$

$$\text{where } E_{HP}^{o\prime} = E_{HP}^o + \frac{RT}{2F} \log_e \frac{1}{K_1 K_2 K_3}$$

and $K_1$ is about $1 \times 10^7$, $K_2$ is in the range of from about $1 \times 10^{12}$ to about $1 \times 10^{14}$, $K_3$ is about $1 \times 10^7$, and $E_{HP}^{o\prime}$ is about 450 millivolts.

4. A method for determining the hydrogen sulfide gas concentration in gaseous equilibrium with a soluble sulfide containing well drilling mud, comprising the steps of
   measuring hydrogen ion concentration in said mud to provide an output signal having an electrical potential which is a function of hydrogen ion concentration,
   measuring sulfide ion concentration in said mud to provide an output signal having an electrical potential which is a function of sulfide ion concentration, and
   subtracting said signal representative of sulfide electrode potential from a signal representative of hydrogen ion electrode potential to provide a difference output signal which varies as a function of the gaseous hydrogen sulfide equilibrium concentration.

5. A method in accordance with claim 4 further including the step of combining a signal representative of a predetermined compensation potential value with said sulfide ion representative signal and said hydrogen ion representative signal such that said difference signal is logarithmically proportional to gaseous hydrogen sulfide equilibrium concentration.

6. A method in accordance with claim 4 wherein said difference output signal is a logarithmic function of the gaseous hydrogen sulfide equilibrium concentration of said mud substantially as follows:

$$\mathrm{Log}_e \text{ (ppm H}_2\text{S gas)} = (E_{HP} - E_{HP}^{o\prime}) \frac{2F}{RT}$$

$$\text{where } E_{HP}^{o\prime} = E_{HP}^o + \frac{RT}{2F} \log_e \frac{1}{K_1 K_2 K_3}$$

and $K_1$ is about $1 \times 10^7$, $K_2$ is in the range of from about $1 \times 10^{12}$ to about $1 \times 10^{14}$, $K_3$ is about $1 \times 10^7$, and $E_{HP}^{o\prime}$ is about 450 millivolts.

7. In a method for determining the H$_2$S hazard potential of well drilling mud by subtracting from a temperature dependent signal representing hydrogen ion electrochemical potential of said mud, a temperature dependent signal representing sulfide ion electrochemical potential of said mud to provide a temperature dependent HP signal which is a function of gaseous H$_2$S equilibrium concentration of said mud, the improvement comprising
   providing temperature compensation for said temperature dependent HP signal by adjusting the gain of said HP signal about its isopotential point to provide a temperature compensated HP signal which is compensated about its isopotential point to provide a temperature independent HP signal which does not vary substantially with varying temperature of the mud being measured.

8. A method in accordance with claim 7 wherein said temperature compensation is provided by normalizing said temperature dependent HP signal to its isopotential point by applying an isopotential point-normalizing bias value thereto, adjusting said gain in response to the temperature of said mud, and subsequently removing the previously applied bias value from said resulting temperature compensated HP signal.

9. A method according to claim 7 wherein said temperature dependent HP signal is an electrochemical potential signal $E_{HP}$ substantially defined as:

$$E_{HP} = E_{pH} - E_S =$$

where $E_{pH}$ is the electrochemical potential of a pH electrode in said mud with respect to a reference electrode, and $E_S =$ is the electrochemical potential of a sulfide ion electrode in said mud with respect to said reference electrode.

10. In apparatus for determining H$_2$S hazard potential of well drilling mud including means for subtracting from a temperature dependent signal representing hydrogen ion electrochemical potential of said mud, a temperature dependent signal representing sulfide ion electrochemical potential of said mud to provide a temperature dependent HP signal which is a function of gaseous H$_2$S equilibrium concentration of said mud, the improvement comprising means for providing temperature compensation for said temperature dependent HP signal by adjusting the gain of said HP signal about its isopotential point to provide a temperature compensated HP signal which is compensated about its isopotential point to provide a temperature independent HP signal which does not vary substantially with varying temperature of the mud being measured.

* * * * *